US009005211B2

(12) United States Patent
Brundobler et al.

(10) Patent No.: US 9,005,211 B2
(45) Date of Patent: Apr. 14, 2015

(54) NAVIGATED APPLICATION GUIDE FOR TARGETED SPINAL DRUG DELIVERY

(75) Inventors: Matthias Brundobler, Münich (DE); Christian Lechner, Jesenwang (DE)

(73) Assignee: Brainlab AG, Feldkirchen (DE)

( * ) Notice: Subject to any disclaimer, the term of this patent is extended or adjusted under 35 U.S.C. 154(b) by 1311 days.

(21) Appl. No.: 11/962,140

(22) Filed: Dec. 21, 2007

(65) Prior Publication Data

US 2008/0154262 A1 Jun. 26, 2008

Related U.S. Application Data

(60) Provisional application No. 60/910,236, filed on Apr. 5, 2007.

(30) Foreign Application Priority Data

Dec. 22, 2006 (DE) ..................... 20 2006 019 649 U

(51) Int. Cl.
| | | |
|---|---|---|
| A61B 17/58 | (2006.01) | |
| A61B 17/60 | (2006.01) | |
| A61F 2/00 | (2006.01) | |
| A61B 19/00 | (2006.01) | |
| A61B 17/00 | (2006.01) | |
| A61B 17/34 | (2006.01) | |

(52) U.S. Cl.
CPC ............... *A61B 19/26* (2013.01); *A61B 19/201* (2013.01); *A61B 19/5244* (2013.01); *A61B 19/56* (2013.01); *A61B 2017/00261* (2013.01); *A61B 2017/3407* (2013.01); *A61B 2019/5483* (2013.01)

(58) Field of Classification Search
CPC .............................. A61B 19/201; A61B 19/26
USPC ............................................ 606/96, 324, 130
See application file for complete search history.

(56) References Cited

U.S. PATENT DOCUMENTS

| | | | |
|---|---|---|---|
| 6,719,757 B2 | 4/2004 | Neubauer et al. | |
| 6,738,657 B1 * | 5/2004 | Franklin et al. ................ | 600/429 |
| 6,837,892 B2 | 1/2005 | Shoham | |
| 6,887,247 B1 * | 5/2005 | Couture et al. .................. | 606/96 |
| 2003/0149430 A1 * | 8/2003 | Ferrante et al. .................. | 606/59 |
| 2004/0267284 A1 * | 12/2004 | Parmer et al. .................. | 606/130 |
| 2005/0165281 A1 * | 7/2005 | Ravikumar et al. ............ | 600/204 |
| 2008/0300465 A1 * | 12/2008 | Feigenwinter et al. ........ | 600/201 |

* cited by examiner

*Primary Examiner* — David Bates
(74) *Attorney, Agent, or Firm* — Tucker Ellis LLP

(57) ABSTRACT

An apparatus and method for positioning a guide tube fixation device at a spinal structure of a patient are provided. The method includes attaching an attachment element to the spinal structure, attaching a guide tube to the attachment element, wherein said guide tube is calibrated prior to attachment, and navigating a part of the guide tube to a predetermined location relative to a target region of the patient. The apparatus includes an attachment device for attaching to the spinal structure, a joint attached to the attachment device, and a guide tube holding device attached to the joint and operable to hold and/or guide a guide tube, said guide tube configured to guide a cannula, needle and/or fluid to a desired site or location.

15 Claims, 9 Drawing Sheets

NAVIGATED APPLICATION GUIDE FOR TARGETED SPINAL DRUG DELIVERY

RELATED APPLICATION DATA

This application claims priority of U.S. Provisional Application No. 60/910,236 filed on Apr. 5, 2007, which is incorporated herein by reference in its entirety.

FIELD OF THE INVENTION

The present invention relates to an application guide and, more particularly, to a guide tube fixation device for fixing a guide tube in the area of the spinal cord, the use of such a guide tube fixation device for guiding a needle or cannula, and a method for positioning such a guide tube fixation device at a structure, such as a vertebra.

BACKGROUND OF THE INVENTION

Typical vertebral column surgical procedures include vertebral fusion, insertion of implants such as pedicle screws, discography, percutaneous disectomy, or the like. These procedures typically require a large invasive operation that exposes the patient to a high risk of infection, excessive trauma, blood or fluid loss, post operative pain, scaring, and lengthy recovery time.

Some difficulties relating to surgery on the vertebral column include, for example, micro-movement of the vertebral column and of vertebral bodies to each other (which may be a risk for injuring extremely delicate nerve tissue or the spinal cord). Another difficulty encountered in vertebral column surgical procedures is the limited operating room space available to the surgeon. Such space limitations are typically due to relatively large support equipment, such as C-arm X-ray devices, that are in the operating room and used during such procedures. Furthermore, the patient and operating room staff are sometimes exposed to large doses of radiation because these procedures require repeated X-raying and/or fluoroscopy of the surgical site to enable the surgeon to view the position of surgical tools or implants relative to non-visible body parts.

If injuries of the spinal cord are treated, drugs should be delivered as precise and accurate as possible. For example Cordaneurin® from NEURAXO Biopharmaceuticals GmbH can be applied to provoke recovery of sensory and motor function of the spinal nerves, which has been already successfully demonstrated in pre-clinical studies.

U.S. Pat. No. 6,837,892 B2 discloses a miniature surgical robot and a method for using such robot, wherein the miniature surgical robot can be directly attached to a bone of a patient. Two-dimensional X-ray images of the robot on the bone can be registered, for example, with three-dimensional CT images of the bone. This locates the robot precisely on the bone of the patient. The robot then can be directed to pre-operatively determined positions based on a plan devised by the surgeon. The robot then can move to the requested surgical site, and a sleeve can be aligned according to the plan such that the surgeon can insert a surgical tool (e.g., a screwdriver, drill bit, or Kirschner wire) into the sleeve. Via the sleeve, the tool can be aligned with the area so as to conduct the operation percutaneously or in traditional open procedures.

SUMMARY OF THE INVENTION

A guide tube fixation device is provided for attaching or fixing a guide tube at a structure, preferably a body structure or a bone, such as a vertebra, to deliver a substance to a preferably predefined site or location in the area of the spinal cord. The guide tube fixation device includes an attachment element, such as a clamping element or a device having a movable holding element to tense the device against the structure (see, e.g., U.S. Pat. No. 6,719,757 B2 for its teaching regarding moveable spikes). The guide tube fixation device also includes a joint, such as, for example, a ball joint, attached to the attachment element and a guide tube holding device attached to the joint. The guide tube holding device can include, for example, a guide way or hole to hold or guide a guide tube. A cannula or a needle, such as a spinal needle, as for example the PAJUNK 24Gx150 mm, can be inserted into or otherwise guided by the guide tube to the desired site or location. Alternatively, a substance itself can be placed within the guide tube (e.g., without using a needle so that the guide tube itself acts as a needle or cannula). Preferably the guide tube fixation device and particularly the guide tube itself are used for the guidance of one or more thin flexible needles so as to enable precise drug delivery directly to a lesion of the spinal cord, wherein the lesion of the spinal cord can be displayed on a navigation screen superposed to data, such as CT data or MR data, of a patient.

To provide the possibility to perform a navigated drug delivery, preferably one or more navigation elements, such as passive or active markers or a reference star comprising at least three reflective markers, can be attached to the guide tube.

The guide tube fixation device also can be used as described in the above application to guide a needle or cannula, such as a spinal needle or a thin and flexible cannula, to a desired location, such as a lesion of the spinal cord.

A system for guiding medical objects includes a guide tube fixation device as set forth herein and an Instrument Calibration Matrix. The Instrument Calibration Matrix includes navigation elements, such as reflective markers, attached thereto and further comprises calibration points or calibration areas, such as drilled holes having different diameters. A tip of a guide tube can be pointed at or inserted into the calibration points/areas to calibrate the guide tube, which can include one or more attached navigation elements such as a reference star.

A method for positioning a guide tube fixation device at a structure, such as a vertebra or spinous process of a vertebra is also provided. An attachment element, such as a clamping element, can be attached to the structure and the guide tube then can be calibrated, for example, by using the Instrument Calibration Matrix described herein. Alternatively, a pre-calibrated guide tube, which can be identified, for example, by a specific arrangement of markers attached to the guide tube, can be used. Thereafter the calibrated or pre-calibrated guide tube can be connected or attached to the clamping element, and the front or distal end of the guide tube can be navigated (e.g., by using the navigation elements attached to the guide tube) to a desired location, such as a lesion or a point having a predefined distance from the lesion.

Preferably, the body structure containing the area to which the distal end of the guide tube (the navigated portion of the guide tube) is to be placed is examined before attaching the clamping element to the body structure. For example, an MR or a CT scan of the body structure and/or the surrounding area can be used to provide data regarding the shape and size of the structure, and this data can be used for navigating the guide tube and particularly a frontal or distal tip of the guide tube to the desired location.

An injury of the spinal cord can be diagnosed, for example, with MR imaging and can be determined and displayed on a navigation system using, for example, iPlan spine®, which is the trade name for a spinal software planning application sold by BrainLAB AG. In the spinal planning software, the injury can be defined and outlined in MR images. The MR data set can be merged to CT images of the spinal cord and the outlined lesion can be transferred to the CT-scan. The software also may enable direct navigation in MR images. The trajectory for the needle, for example, can be previously defined in the software or can be defined intra-operatively. It is also possible that the MR images are directly registered (Fluoro to MRI registration) with the outlined lesion.

The application guide for the spinal needle can be directly attached to a spinal vertebra or spinous process from the posterior near an identified lesion of the spinal cord. After the registration of the patient's CT data set, as for example a region-based surface matching of the patient's CT data set, dorsal fixation and laminectomy at the region of the spinal lesion, the guide tube of the application guide can be manually placed at the predefined spinal lesion under navigational control and can be fixed at the intended position at the posterior or proximal side or end of the guide tube. Afterwards a spinal needle for drug delivery can be inserted through the guide tube and a drug, such as Cordaneurin®, can be applied to the lesion of the spinal cord over a specified period of time, as for example for about 10 to 15 minutes.

It is preferred that the guide tube, once navigated with its distal tip to the desired location, can be fixed or attached in the desired position to have a defined and fixed relationship with respect to the structure. This can be done, for example, by a joint or joint element that can be adjusted or locked by a screw such that the fixed positional relation between the distal tip of the guiding tube and the structure can be established. Now a needle or cannula can be inserted into the guide tube and can be guided therein so that the tip of the needle (e.g., a spinal needle) exits the distal opening of the guide tube to deliver a substance to a desired location.

The spinal needle can be connected to a holding element that can include an adapter element (or the holding element itself may be the adapter element) so as to enable the needle to be connected to a source of the drug to be delivered. This holding element can limit the insertion of the spinal needle into the guide tube, for example, by abutting at an insertion opening of the guide tube. In the fully inserted position of the spinal needle, the spinal needle can be fixed or attached to the guide tube, for example, by using a fixation element, such as a fixation flap. After the spinal needle has been inserted into and fixed on the guide tube (the distal tip of which was navigated to the desired location), the injection or infusion of a desired substance, such as Cordaneurin®, can be performed.

Thus, the method and apparatus provide an accurate and stable placement and guidance of a specified thin, long and flexible spinal injection needle to a specific area of the lesion. The lesion at the spinal cord can be accurately determined on MR images and can be displayed on a navigation system wherein an MRI data set is superposed on a CT data set of the patient. A software package sold by BrainLAB AG under the trade name VectorVision® spine may be used in conjunction with the method and apparatus.

Since the application guide can be directly placed to the vertebra nearest to the lesion of the spinal cord, any patient movements can be compensated for and it can be assured that the drug is accurately injected to the intended area during a specified period of time. This eliminates the need for any other placement of the thin and flexible needle, which would lead to a less stable and less accurate application drug delivery.

The apparatus and method can be used in connection with planning software to define a distribution pattern of the injected substance(s), such as drugs, cultured cells, stem cells, genetic repair cells, etc.

Although the invention is described with reference to the spinal cord, a substance can be injected or infused to other anatomical regions of the spine and elsewhere, such as for example disc repair with cultured disc cells into the disc.

BRIEF DESCRIPTION OF THE DRAWINGS

The forgoing and other features of the invention are hereinafter discussed with reference to the drawings.

DETAILED DESCRIPTION

Figure 1:
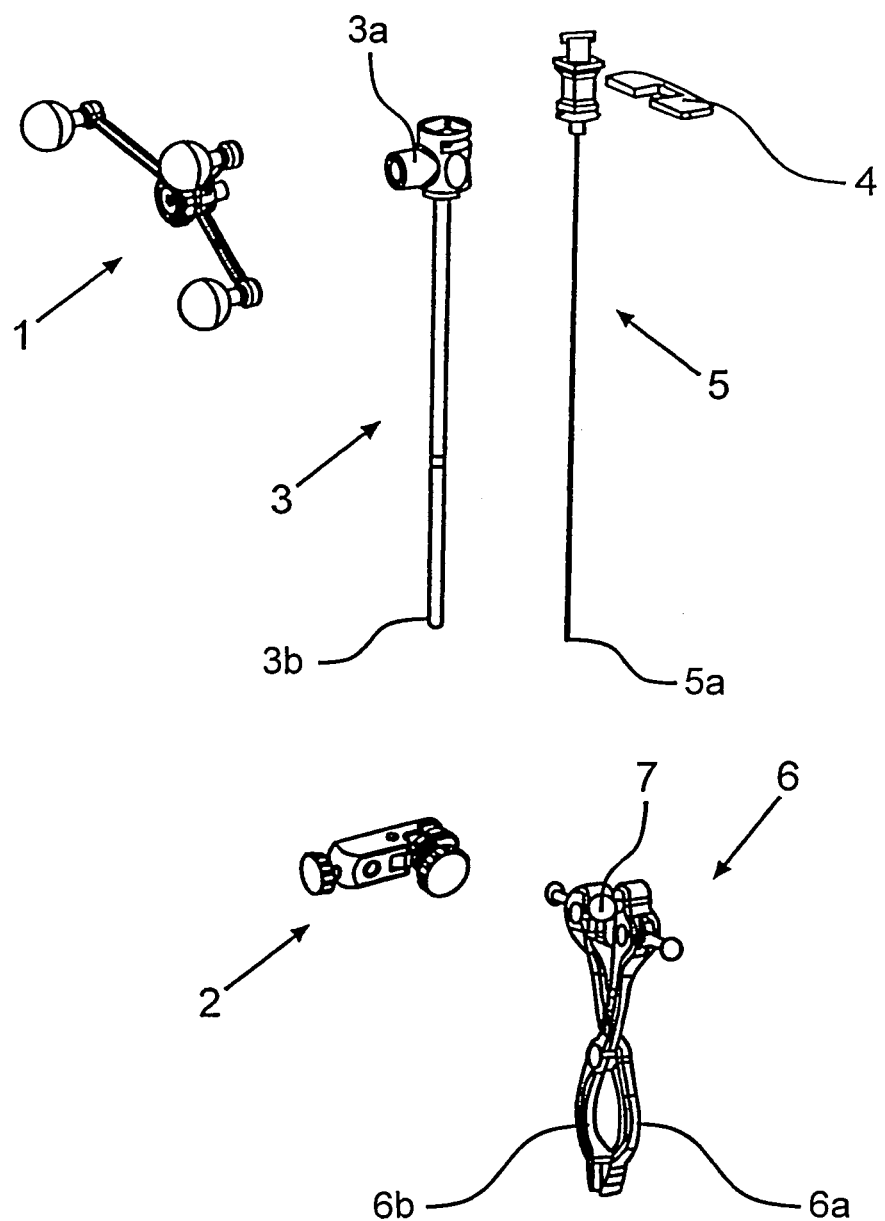
FIG. 1 illustrates an exemplary guide tube fixation device in accordance with the invention.

FIG. 1 shows the elements of an exemplary guide tube fixation device in accordance with the invention. A fixation clamp 6 includes two clamp jaws 6a and 6b and a centrical threaded rod to tension the jaws 6a and 6b. The clamp 6 also includes a sphere 7 to be used as a ball joint sphere, on which a ball joint unit 2 is attached so as to enable adjustment of a distal tip 3b of the guide tube 3 and, thus, of a spinal needle 5 guided by the guide tube 3. The guide tube 3 can be inserted through a hole of the ball joint unit 2 and can include a connecting element 3a for attaching a reference star 1 (e.g., the connecting element 3a can include an instrument adapter star having for example a StarLink interface). A spinal needle 5 can be guided through the guide tube 3 until the distal tip 5a of the spinal needle 5 exits the distal or frontal end 3b of the guide tube 3. A position of the spinal needle 5 can be fixed to the guide tube 3 by means of a fixation flap 4.

Figure 2:
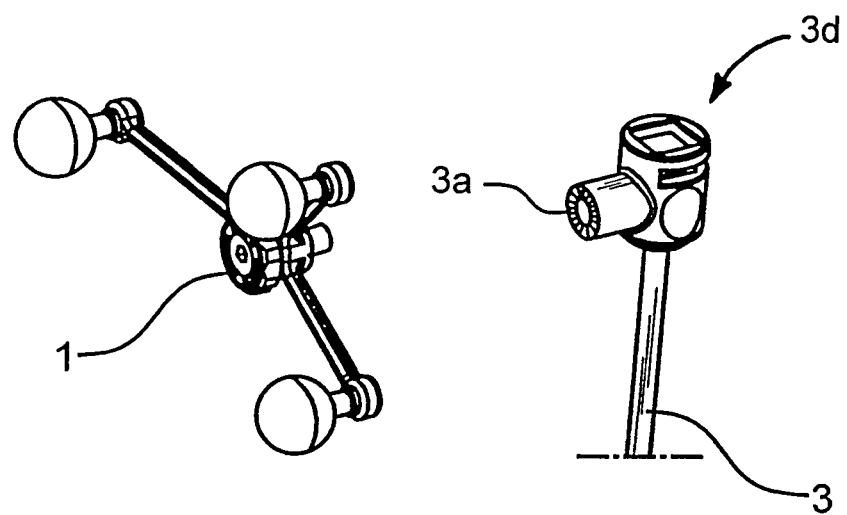
FIG. 2 is an enlarged view of a guide tube and a marker device.

FIG. 2 shows an enlarged view of the guide tube 3 having the universal toothed StarLink interface 3a for attachment of the corresponding instrument adapter star 1. This can be used for manual calibration of the guide tube 3 in combination with the Instrument Calibration Matrix 8 shown in FIG. 6. Alternatively, the guide tube 3 can have a star with different geometry that is rigidly fixed relative to the guide tube 3, so that the guide tube can be used as a pre-calibrated instrument.

Figure 3:
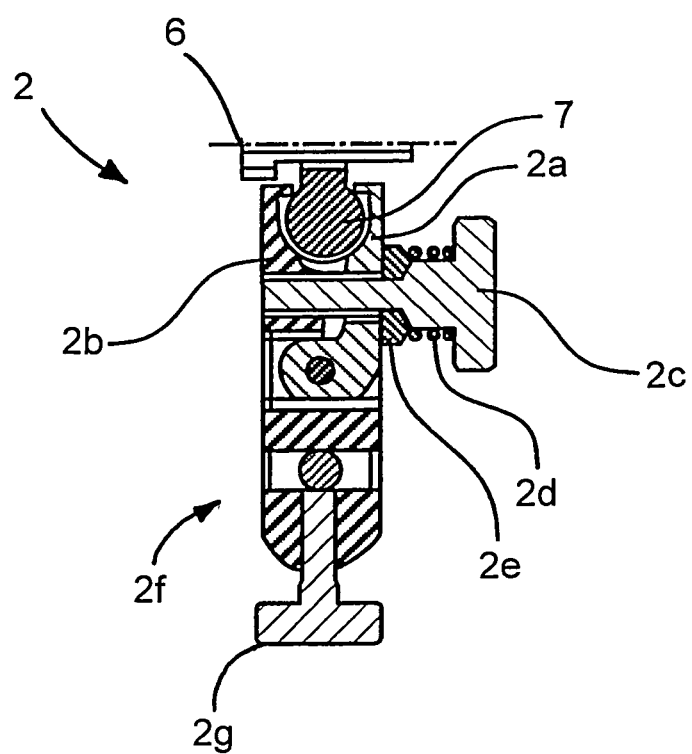
FIG. 3 is a cross sectional view of an exemplary fixation clamp and ball joint unit in accordance with the invention.

FIG. 3 shows in a cross sectional view the fixation clamp 6 and the ball joint unit 2. The fixation clamp 6 has a corresponding sphere 7 for the ball joint interface. The ball joint unit 2 has two corresponding clamps or brackets 2a and 2b for fixation to the sphere 7. The ball joint unit 2 enables the guide tube fixation device to be adjusted in multiple three-dimensional degrees of freedom so as to sufficiently and exactly adjust the guide tube 3 to the intended lesion of the spinal cord. After adjustment, the ball joint unit 2 can be rigidly fixed using the fixation device 2c (e.g., a screw fastener or the like). For proper fixation, a wrench, screw driver, or other tool can be used to manipulate the fixation device 2c so as to provide sufficient force to fix the ball joint relative to the fixation clamp 6.

Operatively coupled to the fixation device 2c are a spring 2d and washer 2e. The spring and washer can facilitate attachment of the ball joint unit 2 to the sphere 7. For example, the spring 2d exerts a force on the brackets 2a and 2b, which in turn exert a force on the sphere 7. Thus, even though the fixation device 2c may not create sufficient force to prevent movement of the ball joint unit 2 relative to the sphere 7 (or possible insufficient force to hold the ball joint unit to the sphere), the spring 2d creates a predetermined force that at least maintains the brackets 2a and 2b in contact with the sphere 7. This predetermined force prevents or minimizes the likelihood that the ball joint unit 2 will detach from the sphere 7 before the fixation device 2c can provide significant holding force. In general, various principles can be feasible for the ball joint design.

The guide tube 3 can be inserted into an opening 2f of the ball joint unit 2 and fixed in place via clamp 2g. This enables the position of the guide tube to be fixed relative to the ball joint unit 2.

Figure 4A:
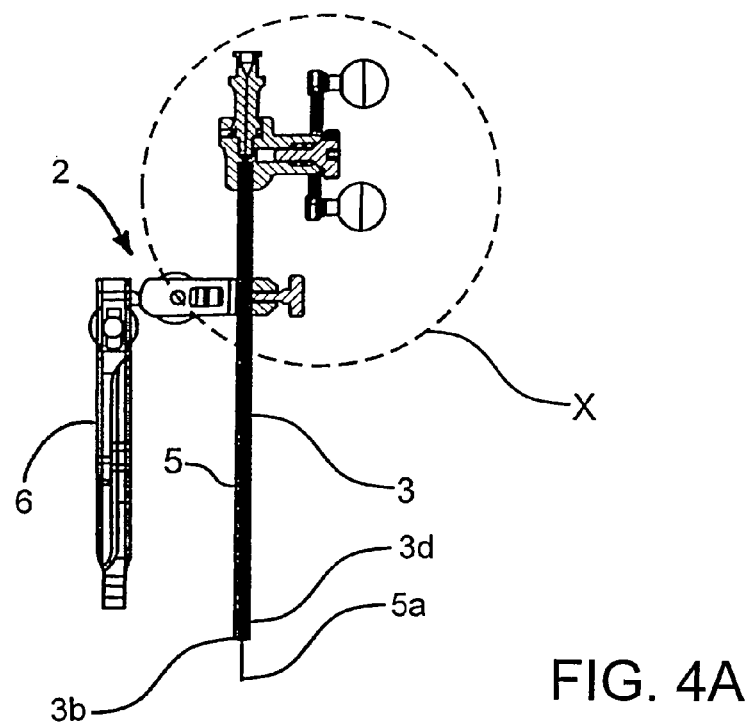
FIG. 4A is a cross sectional view of an exemplary a guide tube and spinal needle.
Figure 4B:
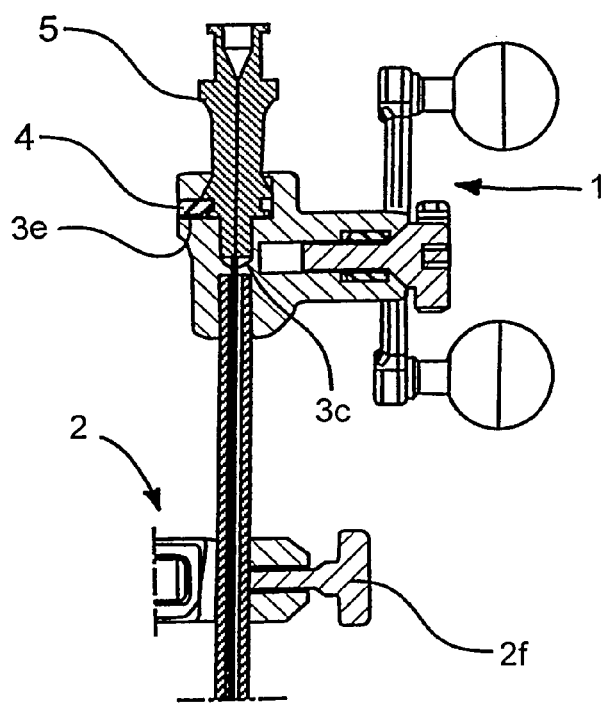
FIG. 4B is an enlarged view of a portion of the device shown in FIG. 4A.

FIG. 4A shows in a cross sectional view the guide tube 3 and the spinal needle 5, wherein the detail X is shown in an enlarged view in FIG. 4B. After navigated adjustment, the guide tube 3 can be fixated using the fixation device 2c of the ball joint unit 2. However, other fixation principles are also possible.

The length and the inner core diameter of the guide tube 3 can be exactly aligned for use in combination with a specified spinal needle, such as the PAJUNK 24Gx150 mm. The spinal needle 5 is thereafter inserted into the guide tube 3 until the end stop 3c prevents further inward movement. Due to the aligned length, it is guaranteed that the tip 5a of the spinal needle 5 extends out of the guide tube 5 by a predefined length (e.g., 12 mm) at the tip 3b of the guide tube 3. This length is estimated to provide and achieve a sufficient penetration depth for injection into the lesion as well as to enable sufficient stability during use with less bending of the thin needle tip.

The spinal needle 5 is precisely guided within the core hole 3d of the guide tube 3, which has a diameter that is within a predetermined tolerance of the spinal needle diameter. For secure fixation of the spinal needle 5 after insertion into the guide tube 3, the guide tube 3 includes slot 3e for use with the fixation flap 4. The fixation flap 4 can be inserted into the slot 3e so as to interface with the spinal needle 5 and prevent the needle 5 from being pushed backwards during the application and drug delivery. It is noted that the tip 3b of the guide tube 3 can have rounded edges so as to minimize the likelihood of injury to the dura or outer surfaces of the spinal cord if accidentally touched during the navigated placement.

Figure 5:
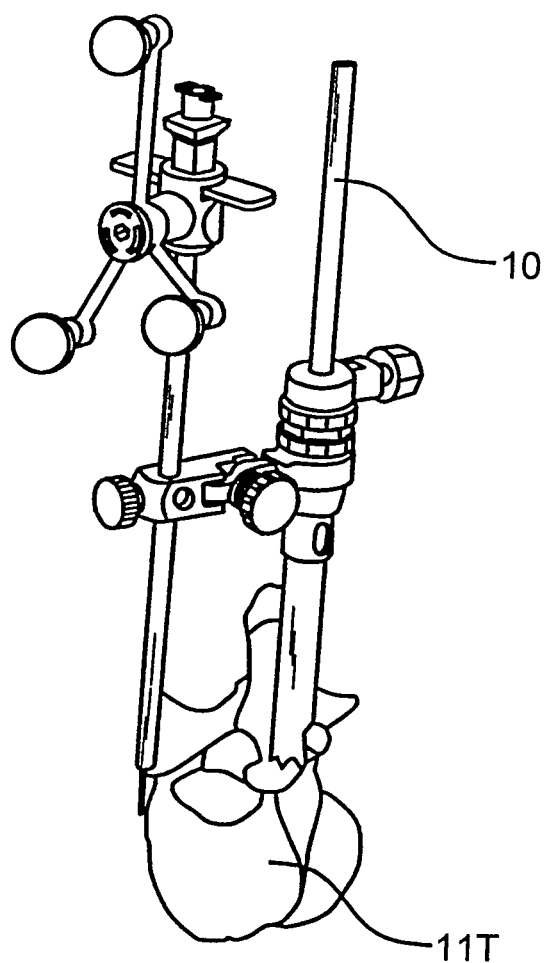
FIG. 5 illustrates another exemplary guide tube fixation device in accordance with the invention.

FIG. 5 shows another exemplary guide tube fixation device in accordance with the invention. In the embodiment of FIG. 5, the application guide is rigidly fixated to a Schanz-screw or a pedicle screw 10, which is inserted into the pedicle and used for the spinal stabilisation. The shown 1-pin fixation principle is described in U.S. Pat. No. 6,719,757, which is hereby incorporated by reference in its entirety.

Before starting the drug injection, a spinal fixation at the area of the spinal lesion can be performed using standard spinal implant systems, such as polyaxial pedicle screws and rods. Thus, it is also possible to rigidly attach the application guide to a single rod or as a "bridge-design" clamping to opposing rods attached to the structure, such as the vertebra.

Figure 6:
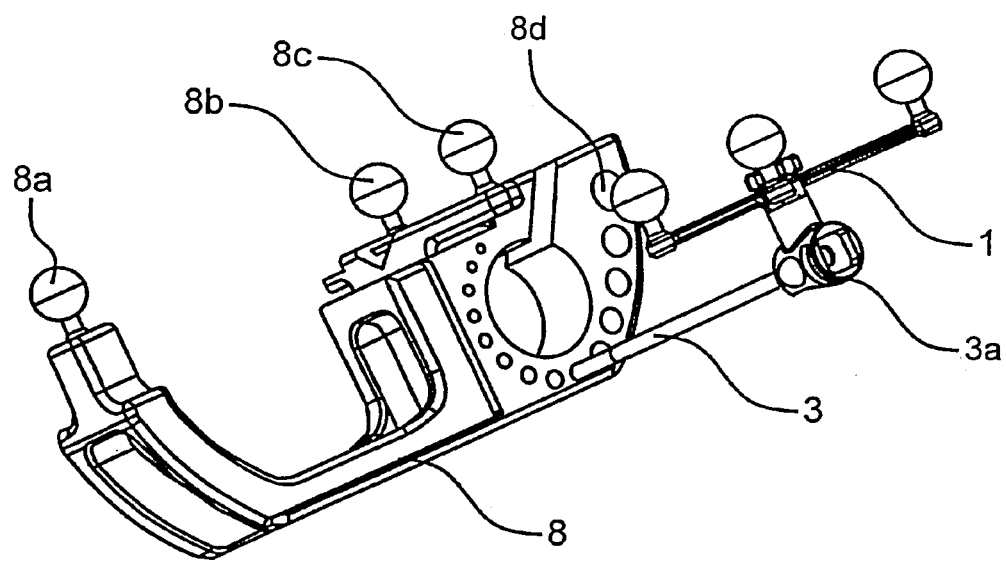
FIG. 6 is an exemplary Instrument Calibration Matrix for calibration of the guide tube.

FIG. 6 shows an embodiment of an Instrument Calibration Matrix 8 comprising three reflective marker spheres 8a-8c attached thereto. Holes or bores 8d of respective different diameters are provided in the Instrument Calibration Matrix 8, wherein the frontal or distal tip 3b of the guide tube 3 can be inserted into the bores 8d to calibrate the guide tube 3 (which has the reference star 1 attached thereto).

Figure 7A:
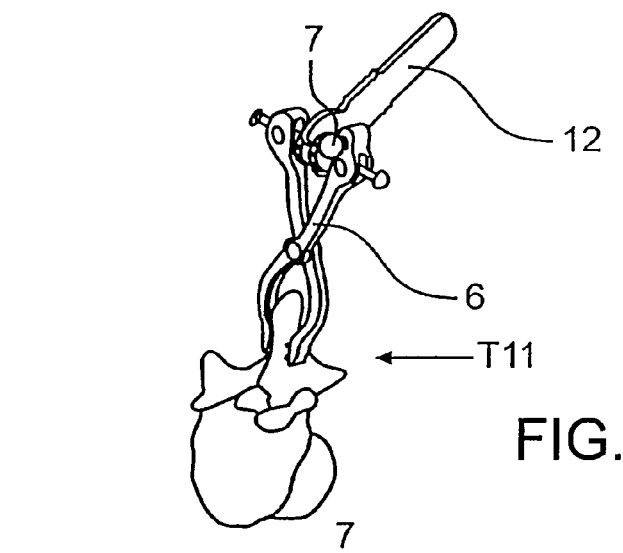
FIGS. 7A-7H illustrate an exemplary method of using the guide tube fixation device in accordance with the invention.
Figure 7B:
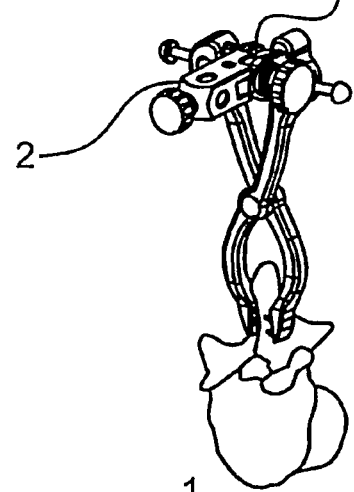
Figure 7C:
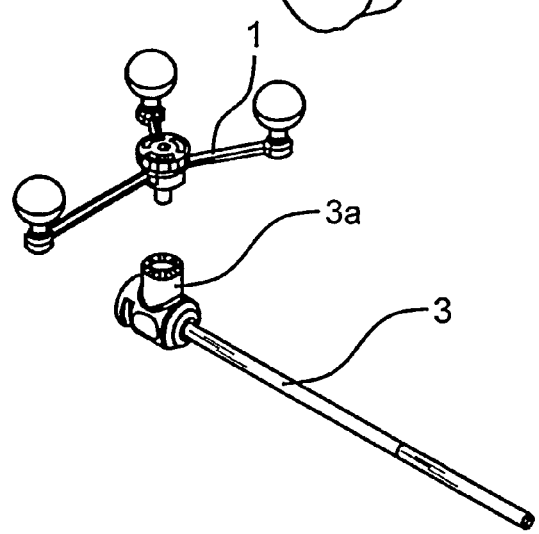
Figure 7D:
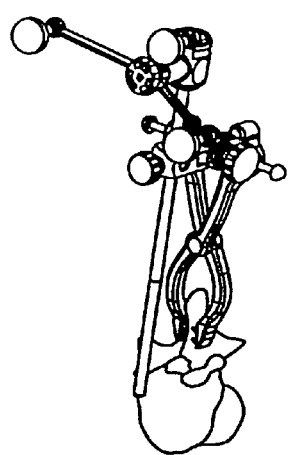
Figure 7E:
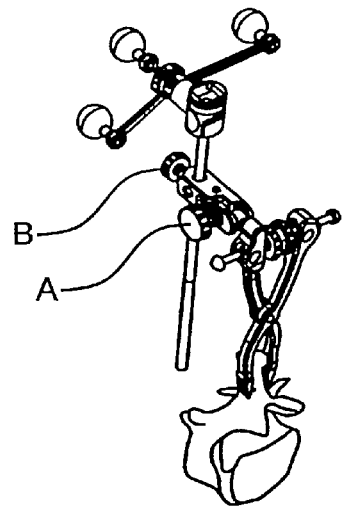
Figure 7F:
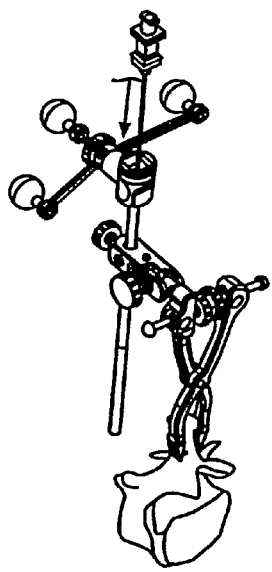

FIGS. 7A to 7H show an exemplary method for positioning a guide tube fixation device at a structure (e.g., spinous process of a vertebra) in accordance with the invention. FIG. 8 is a screen shot of an exemplary navigation system that can be used to navigate the guide tube 3 and/or needle 5.

If, for example, there is a spinal fracture at T10, a navigated or standard dorsal fixation with a spine reference X-clamp attached to T9 or T11 can be performed. The spine reference clamp can be attached preferably to a level closer to the camera, for example T11, and a registration can be performed, preferably a region based surface matching of T10. Afterwards, a Laminectomy can be done at T10. The lesion or injury of the spinal cord at T10, for example, can be displayed on an image output device. Further, and if desired, the lesion or injury can be outlined using a software application and displayed as an overlaid structure on the CT-data used in the Navigation System.

The application guide clamp can be tightly fixed on the spinous process of opposing vertebra T9 or T11 via the spine reference X-clamp, wherein a tool 12 can be used to establish sufficient holding force at the X-clamp. Afterwards, the ball joint connector 2 can be attached to the sphere 7 at the clamp, as shown in FIG. 7B. The star link adapter array 1 can be attached to the guide tube adapter 3a as shown in FIG. 7C, and then manually calibrated with the Instrument Calibration Matrix 8.

A virtual tool tip extension of known pre-defined length (e.g., 12 mm) of the protruding needle tip can be manually adjusted in software so that the real tip position of the later inserted needle 5 can be correctly displayed. Thereafter, the guide tube adapter 3a can be adjusted with the ball-joint unit 2 under navigational control, so that the extended tip displayed on the navigation screen is in the lesion or injury region of the spinal cord as planned. After the correct position has been found, all fixation screws A and B are properly tightened to fix the position of the guide tube 3 as shown in FIG. 7E. Thereafter, as shown in FIG. 7F, the spinal injection needle 5 can be inserted into the guide tube adapter 3a.

Figure 7G:
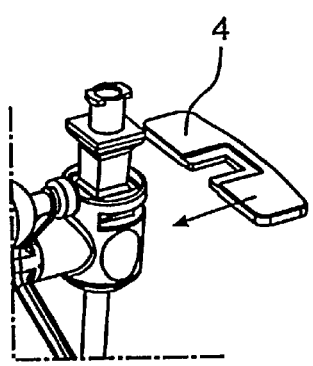
Figure 7H:
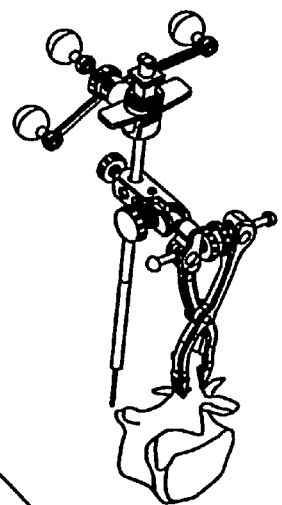
Figure 8:
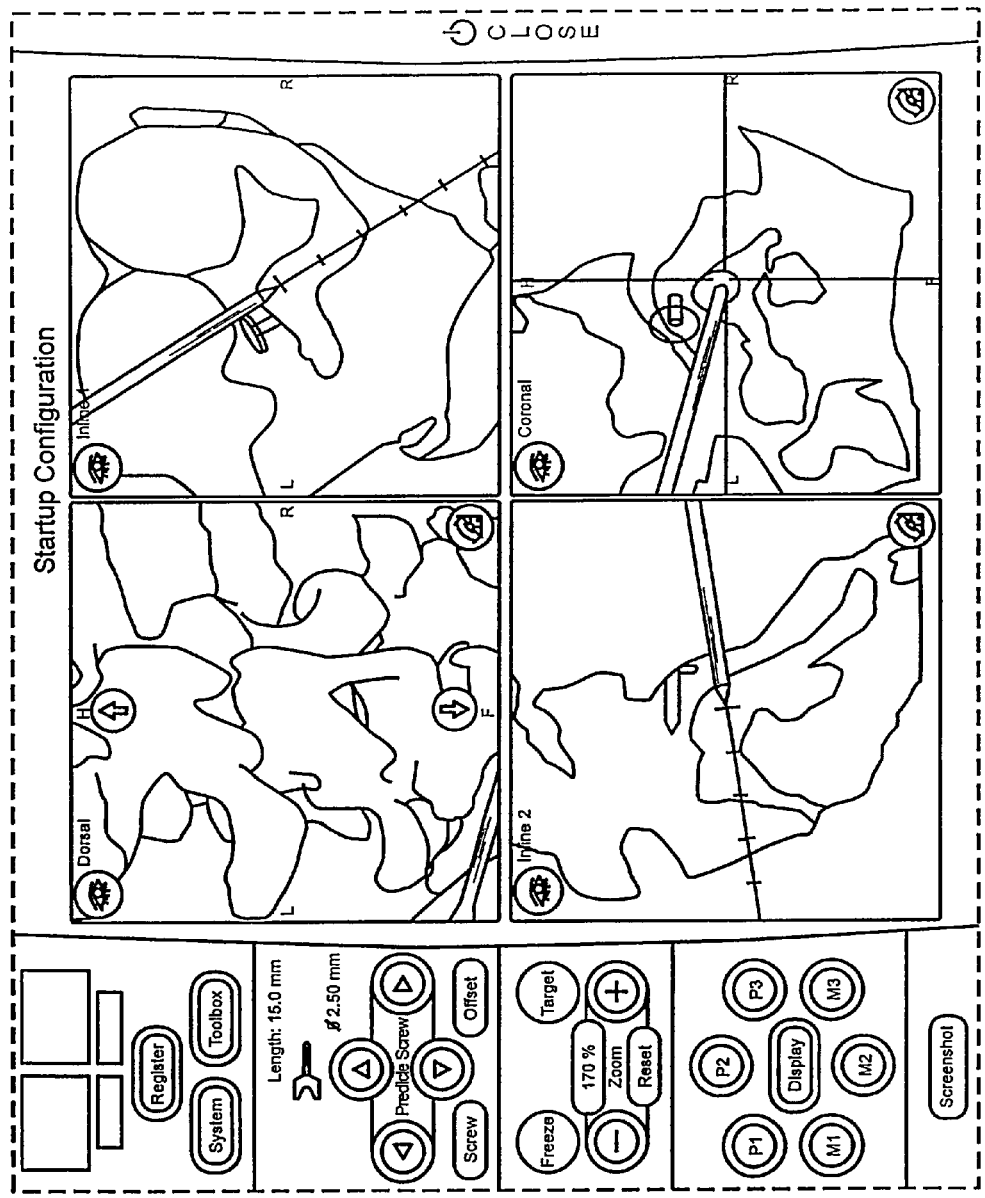
FIG. 8 is a screen shot of an exemplary navigation system used to navigate the guide tube or needle.

As shown in FIG. 7G, the needle flap 4 is attached into the slot of the guide tube adapter 3a in order to properly fixate the spinal injection needle 5. Thereafter, as shown in FIG. 7H, the flexible injection tube for the drug to be delivered is attached to a proximal luer-connector of the spinal injection needle 5 so that the drug can be applied and injected to the lesion or injury at the spinal cord.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A surgical guide tube fixation device for attaching or fixing a guide tube to a spinal structure to deliver a substance to a target region, said guide tube fixation device comprising:
   an attachment device for attaching to the spinal structure, the attachment device comprising a clamp or a clamping element configured to clamp to a spinal structure;
   a joint attached with the attachment device;
   a spinal needle having a length and a diameter;
   a guide tube having a length and an inner core diameter, wherein the guide tube is configured to guide the spinal needle to a desired site or location and the inner core diameter of the guide tube is substantially the same as the diameter of the spinal needle and the length of the spinal needle is aligned with the length of guide tube; and
   a guide tube holding device attached with the joint and operable to hold and/or guide the guide tube, the guide tube holding device comprising a bore configured to receive the guide tube and a fixing device configured to selectively lock and release the guide tube within the bore to selectively prevent and enable movement of the guide tube within the bore.

2. The guide tube fixation device of claim 1, wherein the joint is a ball joint.

3. The guide tube fixation device according to claim 1, further comprising a joint fixation element selectively operable to inhibit or enable movement of the joint.

4. A surgical guide tube fixation device for attaching or fixing a guide tube to a spinal structure to deliver a substance to a target region, said guide tube fixation device comprising:
   an attachment device for attaching to the spinal structure;
   a joint attached with the attachment device;
   a spinal needle having a length and a diameter;
   a guide tube having a length and an inner core diameter, wherein the guide tube is configured to guide the spinal needle to a desired site or location and the inner core diameter of the guide tube is substantially the same as the diameter of the spinal needle and the length of the spinal needle is aligned with the length of the guide tube; and
   a guide tube holding device attached with the joint and operable to hold and/or guide the guide tube, the guide tube holding device comprising a bore configured to receive the guide tube and a fixing device configured to selectively lock and release the guide tube within the bore to selectively prevent and enable movement of the guide tube within the bore,
   wherein the attachment device comprises an attachment portion configured to interface with the spinal structure, and a moveable holding element operatively coupled with said attachment portion, wherein the holding element is operable to adjust a dimension of the attachment portion.

5. The guide tube fixation device according to claim 1, further comprising at least one navigation element attached to the guide tube.

6. A system for calibrating a guide tube in a medical procedure, said guide tube including one or more navigation elements that are trackable by a tracking and/or navigation system, comprising:
   a guide tube fixation device according to claim 1; and
   an Instrument Calibration Matrix comprising
       a) navigation elements attached thereto,
       b) calibration points or calibration areas for contacting or inserting a tip of the guide tube so as to calibrate the guide tube in a medical workspace.

7. The guide tube fixation device of claim 1, wherein the attachment device comprises at least two clamp jaws configured to clamp to the spinal structure.

8. The guide tube fixation device of claim 7, wherein the joint comprises a joint fixation element to hold the joint in a fixed position.

9. The guide tube fixation device of claim 8, wherein the guide tube holding device is configured to be telescopically arranged on the guide tube.

10. The guide tube fixation device of claim 7, further comprising a threaded member operatively coupled to the at least two clamp jaws and configured to effect motion of the at least two clamp jaws relative to each other.

11. The guide tube fixation device according to claim 5, wherein the at least one navigation element comprises a passive marker.

12. The guide tube fixation device of claim 1, wherein the guide tube defines an elongate core hole having an inner diameter along the length thereof and opening on opposite ends of the guide tube, the core hole being configured to conduct the associated fluid therethrough.

13. The guide tube fixation device of claim 4, wherein the guide tube defines an elongate core hole having an inner diameter along the length thereof and opening on opposite ends of the guide tube, the core hole being configured to conduct the associated fluid therethrough.

14. The guide tube fixation device of claim 1, wherein upon full insertion of the spinal needle into one end of the guide tube, the length of the spinal needle is such that the spinal needle extends no further than a predefined length from a complementary end of the guide tube.

15. The guide tube fixation device of claim 4, wherein upon full insertion of the spinal needle into one end of the guide tube, the length of the spinal needle is such that the spinal needle extends no further than a predefined length from a complementary end of the guide tube.

* * * * *